United States Patent [19]

Kieturakis

[11] Patent Number: 5,643,282
[45] Date of Patent: Jul. 1, 1997

[54] SURGICAL INSTRUMENT AND METHOD FOR REMOVING TISSUE FROM AN ENDOSCOPIC WORKSPACE

[76] Inventor: Maciej J. Kieturakis, 372 Beverly Dr., San Carlos, Calif. 94070

[21] Appl. No.: 293,855

[22] Filed: Aug. 22, 1994

[51] Int. Cl.[6] ................................................ A61B 17/24
[52] U.S. Cl. ............................................ 606/114; 606/127
[58] Field of Search ...................... 606/114, 127, 606/170, 171, 205; 403/292, 321, DIG. 8; 604/133

[56] References Cited

U.S. PATENT DOCUMENTS

| | | |
|---|---|---|
| 2,756,752 | 7/1956 | Scherlis ............................... 606/127 |
| 4,191,191 | 3/1980 | Auburn . |
| 4,535,773 | 8/1985 | Yoon . |
| 4,601,710 | 7/1986 | Moll . |
| 4,654,030 | 3/1987 | Moll et al. . |
| 5,116,353 | 5/1992 | Green . |
| 5,147,316 | 9/1992 | Castillenti . |
| 5,147,376 | 9/1992 | Pianetti . |
| 5,190,561 | 3/1993 | Gruber ............................... 606/114 |
| 5,203,773 | 4/1993 | Green . |
| 5,209,736 | 5/1993 | Stephens et al. . |
| 5,217,468 | 6/1993 | Clement ............................. 606/114 |
| 5,224,952 | 7/1993 | Deniega et al. . |
| 5,226,890 | 7/1993 | Ianniruberto et al. . |
| 5,232,451 | 8/1993 | Freitas et al. . |
| 5,258,003 | 11/1993 | Ciaglia et al. . |
| 5,271,380 | 12/1993 | Riek et al. . |
| 5,279,567 | 1/1994 | Ciaglia et al. . |
| 5,346,504 | 9/1994 | Ortiz et al. ......................... 606/192 |
| 5,370,647 | 12/1994 | Gruber .............................. 606/127 |

Primary Examiner—Michael A. Brown
Attorney, Agent, or Firm—Skjerven, Morrill, MacPherson, Franklin & Friel; Norman R. Klivans

[57] ABSTRACT

A surgical instrument is used to remove excised tissue from an insufflated anatomic cavity through a body wall overlying an endoscopic workspace. The instrument includes an elongate tubular sleeve defining an interior bore fore removing a tissue. The tubular sleeve also called a snake is elastic in its transverse sectional dimension so that the interior bore can expand to accommodate the excise tissue as it is slidably withdrawn through the bore. The sleeve is not elastic in the longitudinal direction due to flexible but non-elastic longitudinal elements integrated into or on the wall of the sleeve.

22 Claims, 11 Drawing Sheets

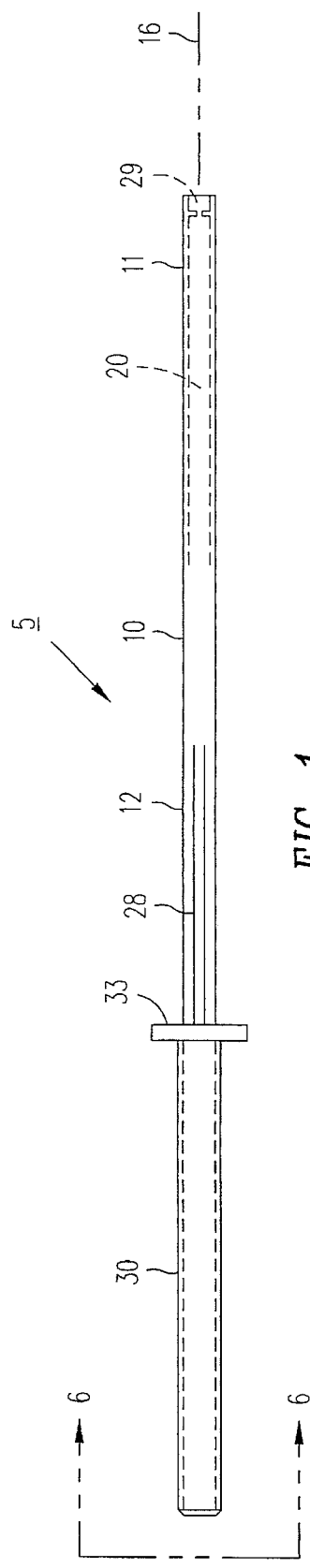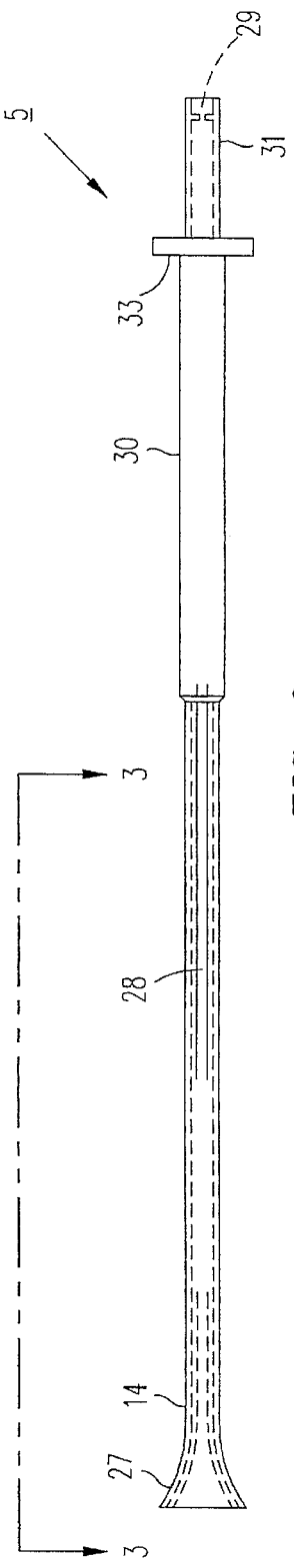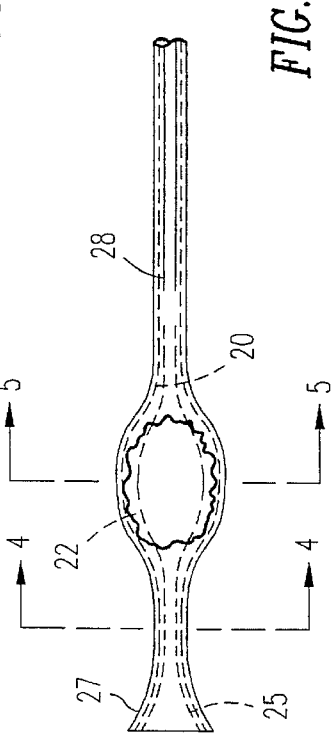

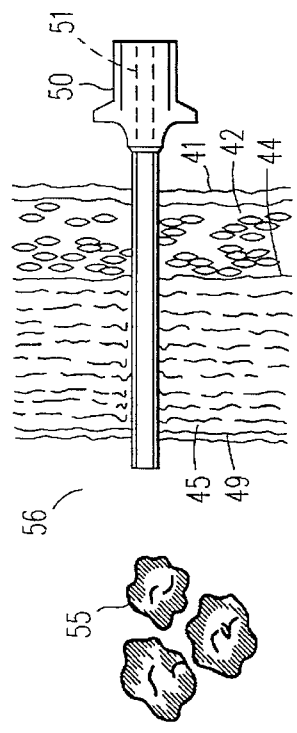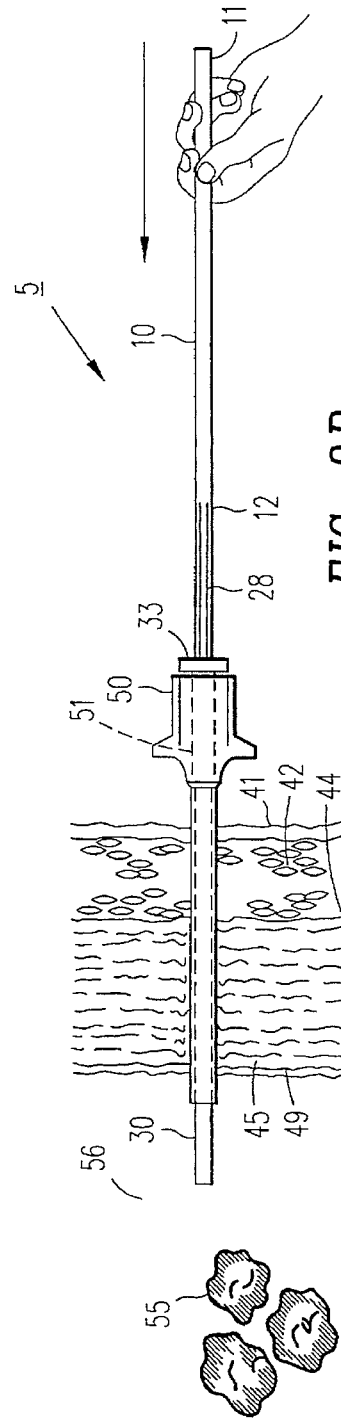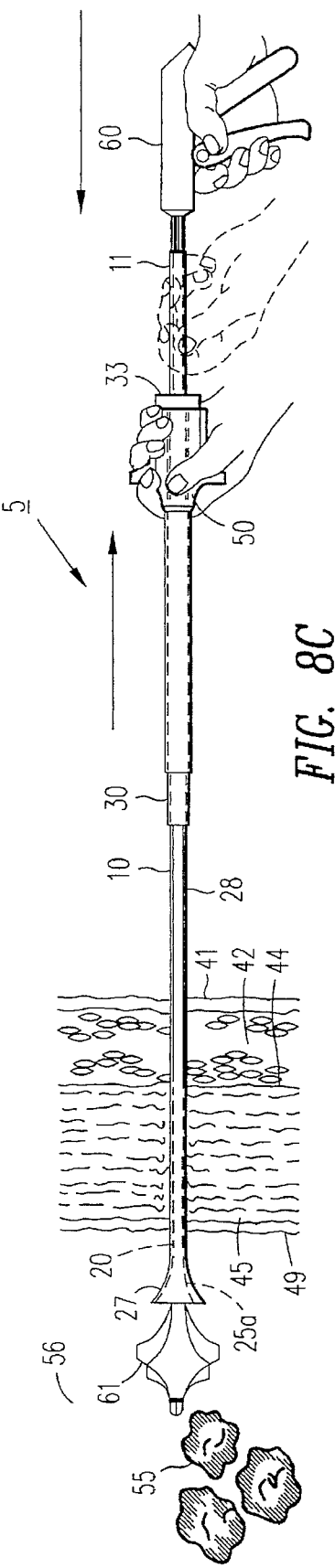

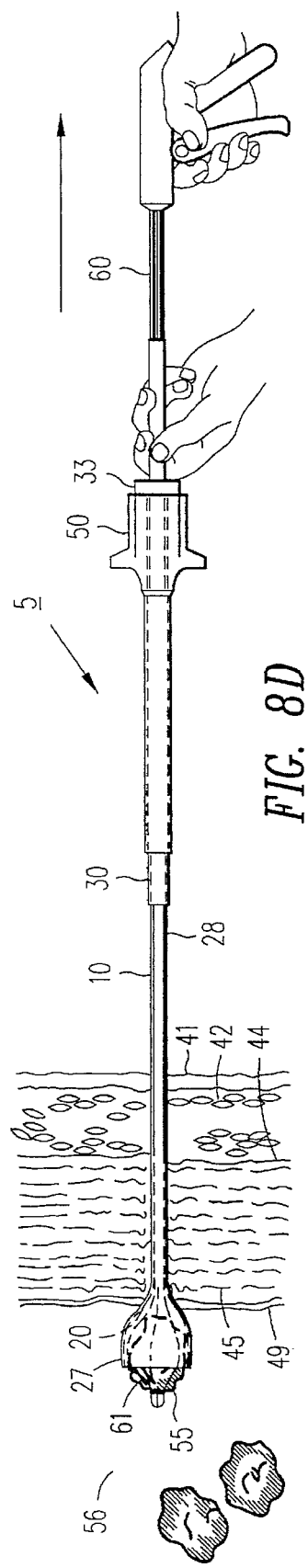
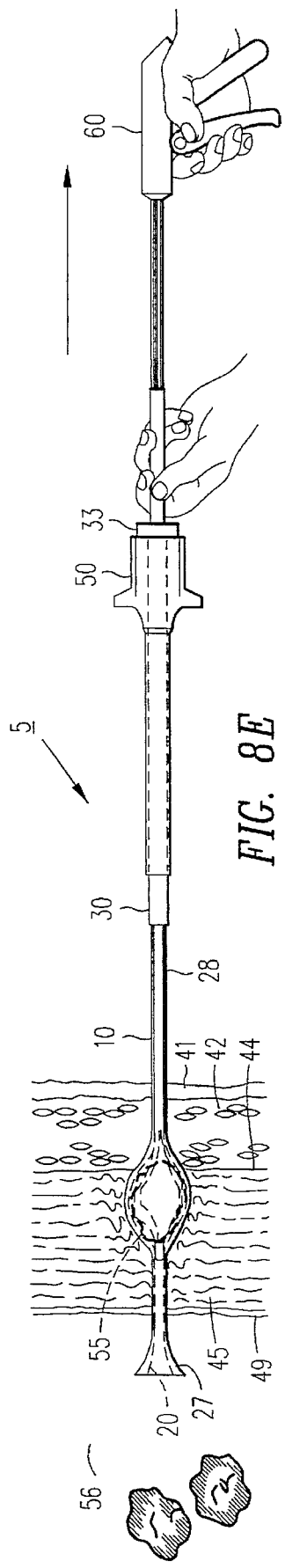
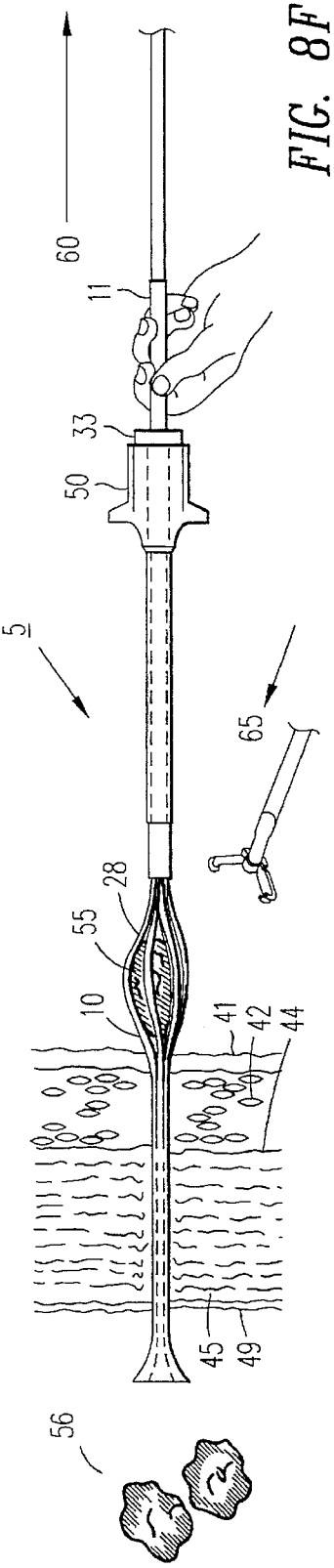

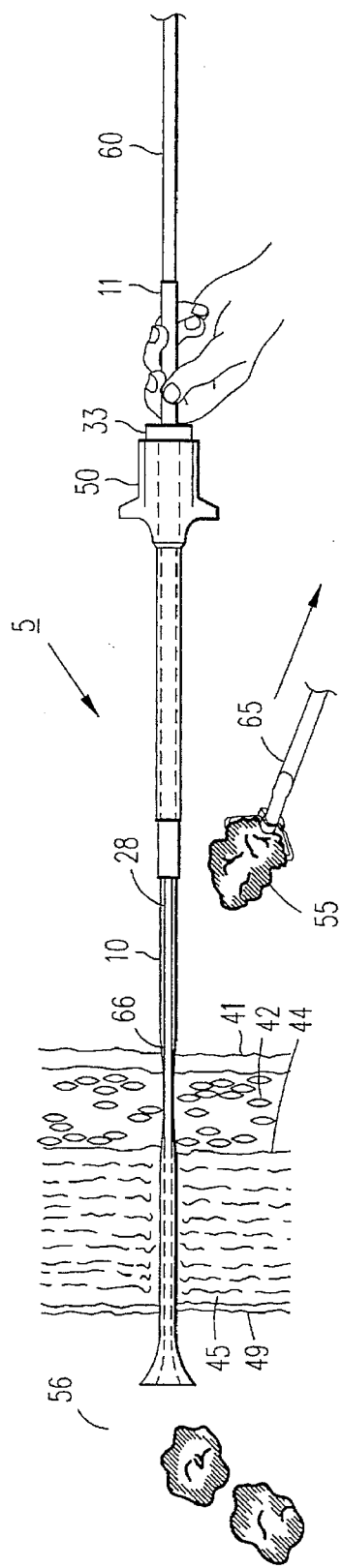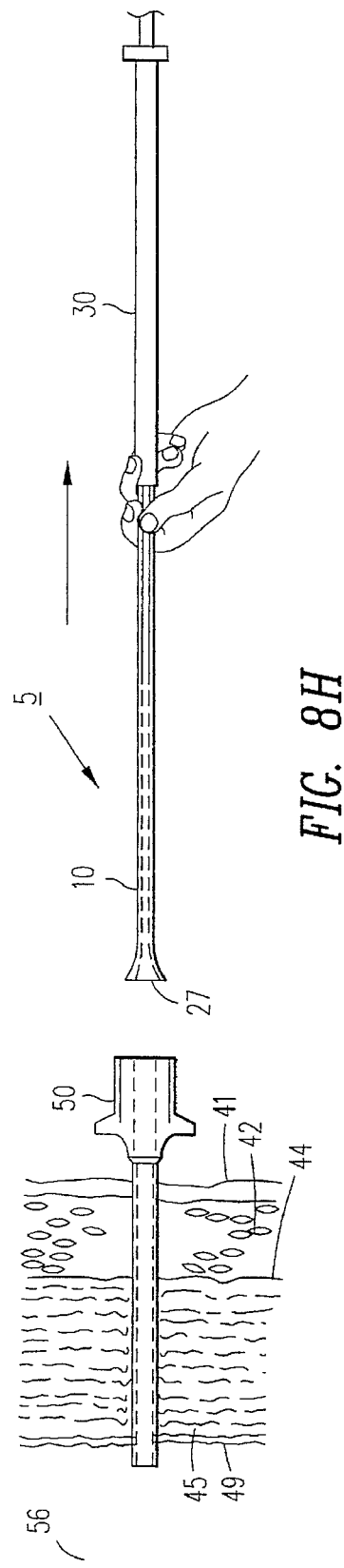

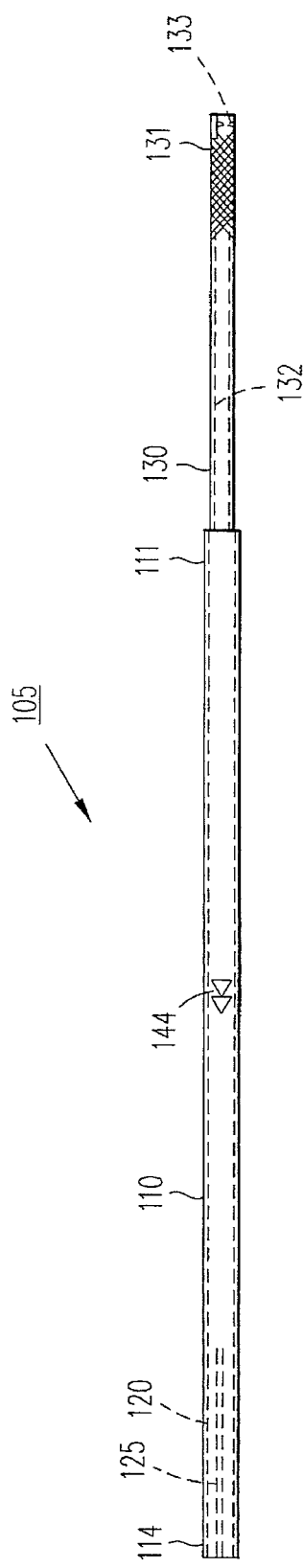
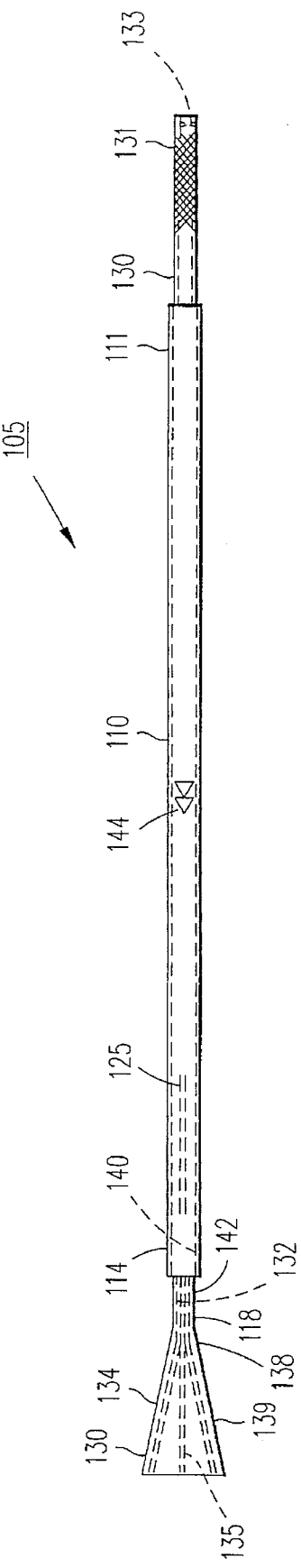
FIG. 9
FIG. 10

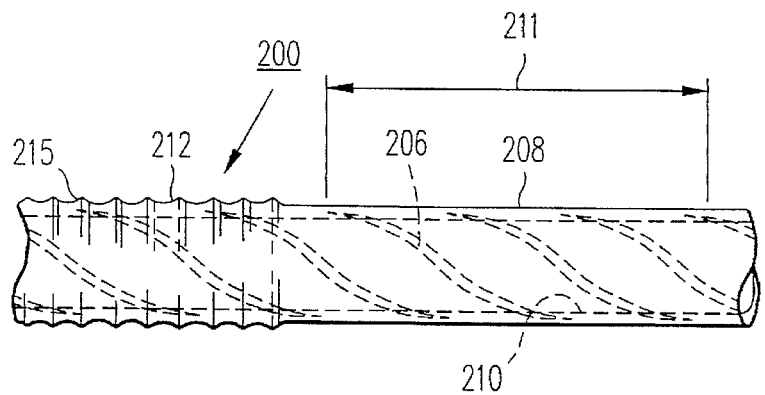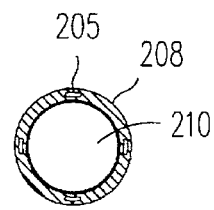
FIG. 12A    FIG. 12B
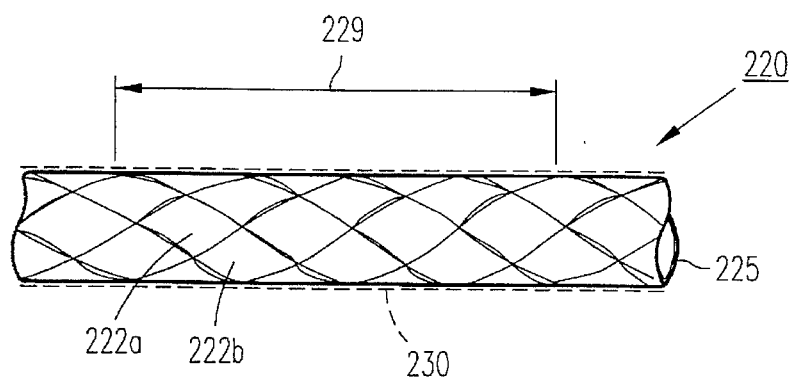
FIG. 13
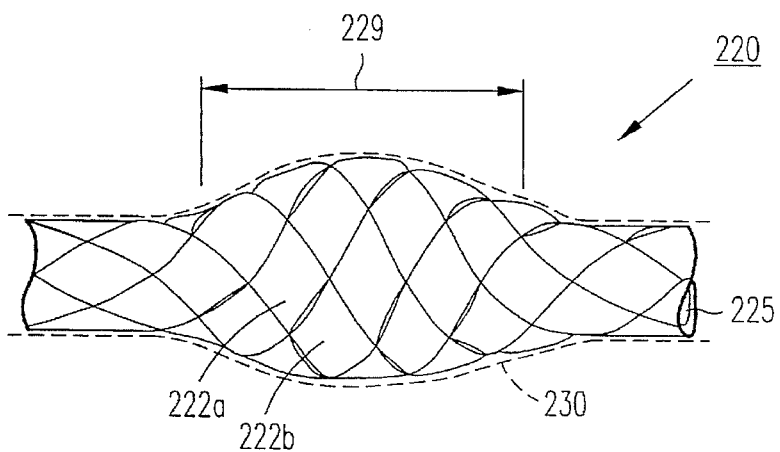
FIG. 14

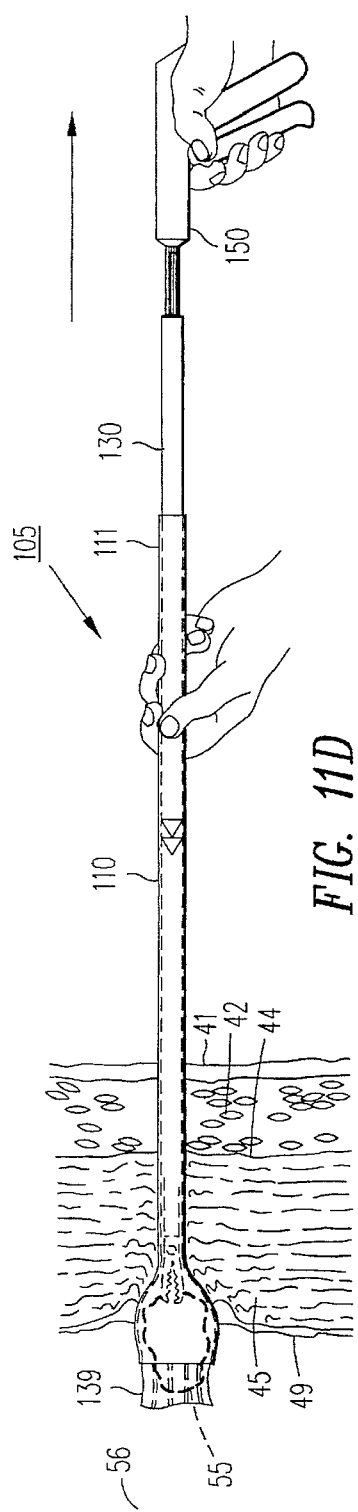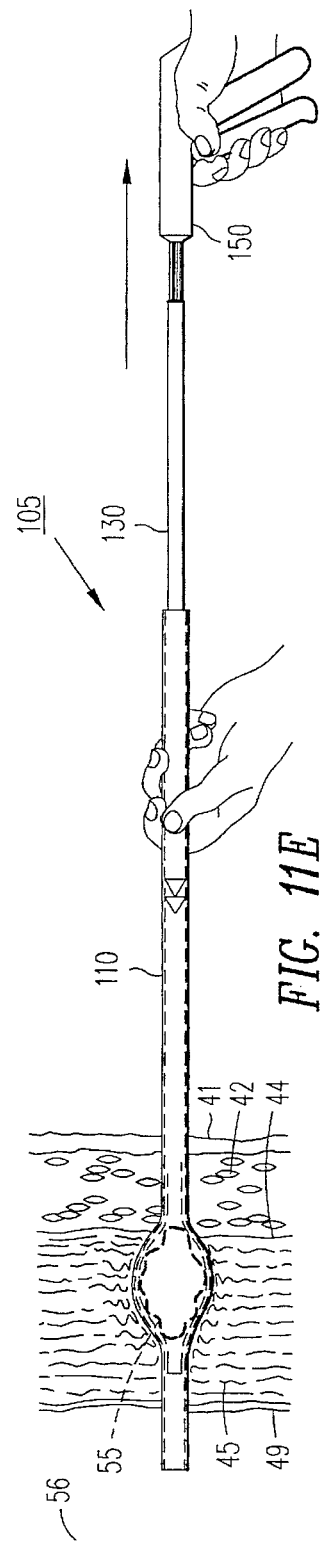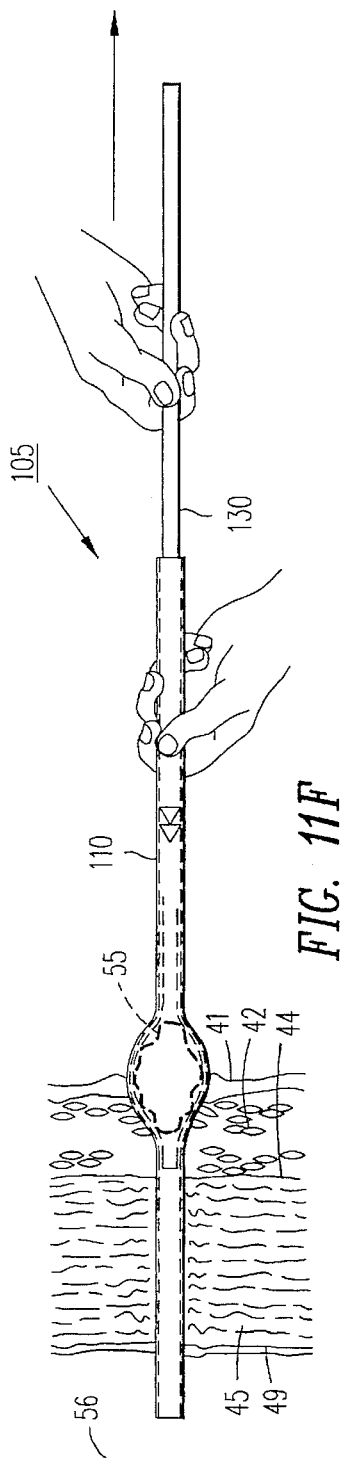

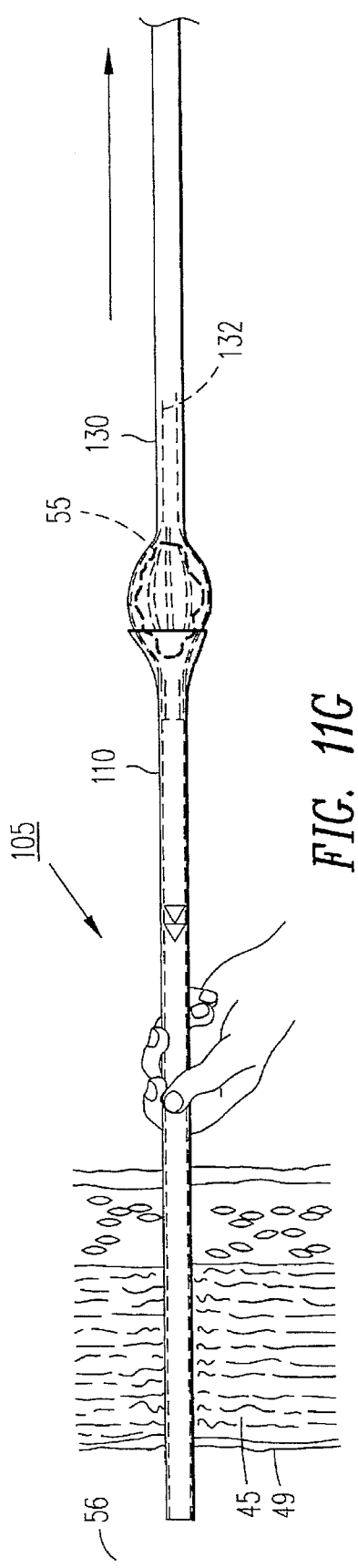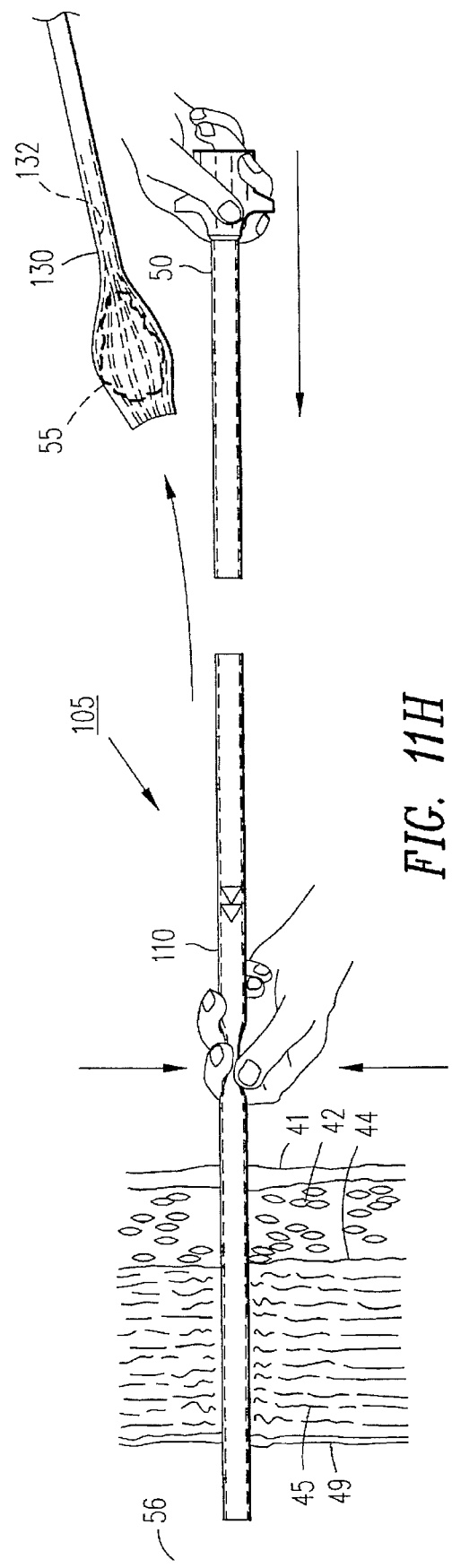

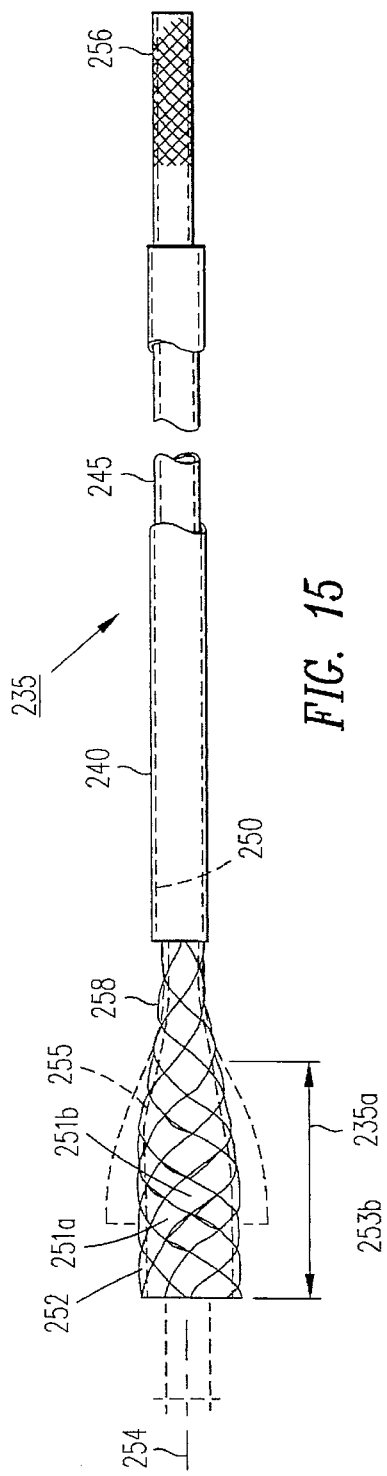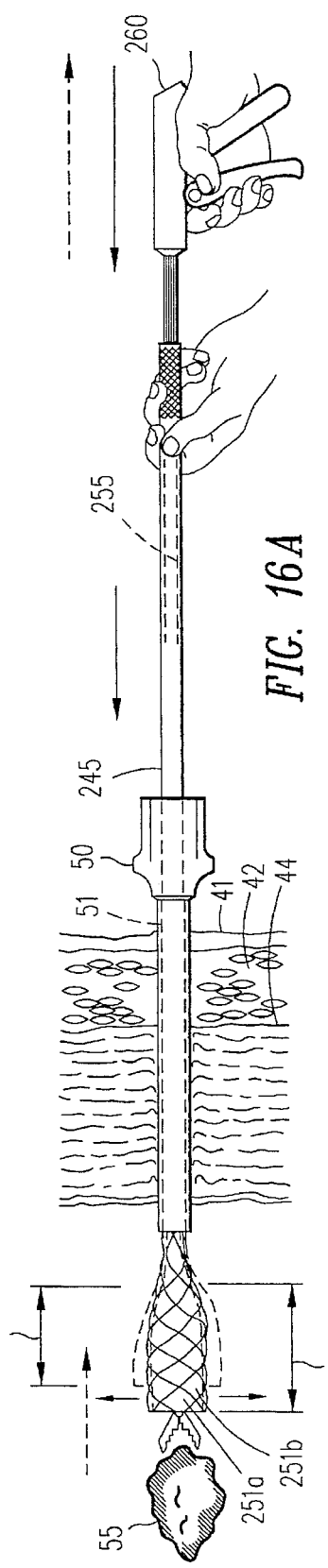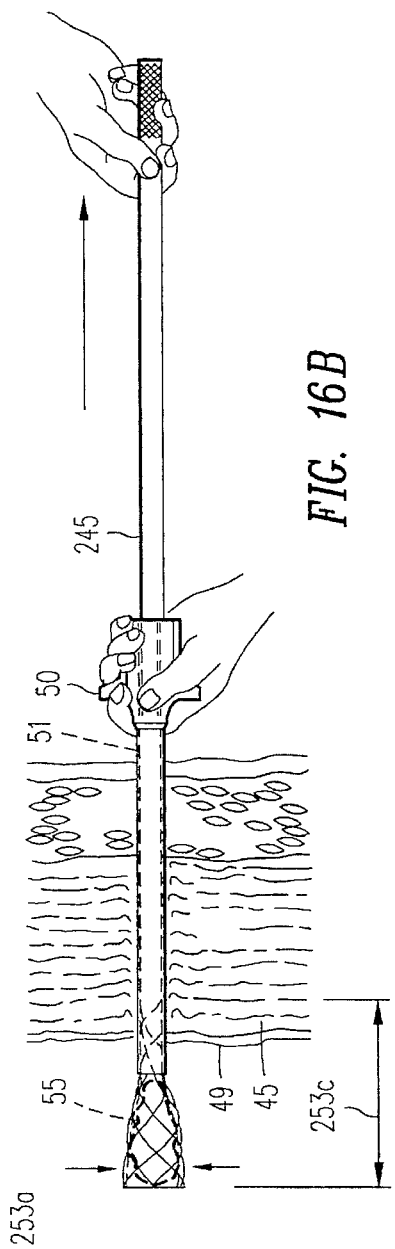

SURGICAL INSTRUMENT AND METHOD FOR REMOVING TISSUE FROM AN ENDOSCOPIC WORKSPACE

BACKGROUND OF THE INVENTION

1. Field of the Invention

This invention relates to surgical instrumentation and more particularly to an instrument and method for removing excised tissue from an insufflated endoscopic workspace in cases in which such tissue has a larger transverse dimension than the incision providing access to the workspace.

2. Description of Prior Art

In a "minimally invasive" endoscopic surgery in an insufflated workspace, for example an insufflated abdominal cavity, it has been found that it is sometimes difficult to remove excised tissue from the workspace. Since instruments are introduced into the workspace typically through 10 mm. diameter cannulas within the abdominal wall, it may not be possible to drag tissue pieces much larger than 10 mm. in cross section through the cannula. The use of larger diameter cannulas is possible but undesirable because of the larger incisions required. Also, dragging tissue through a cannula assembly often contaminates the cannula valve, preventing the valve from sealing insufflation gases within the workspace. A contaminated valve also may contaminate the lens of an endoscope subsequently introduced through the cannula. There is therefore a need for new instruments and methods for removing excised tissue from an endoscopic workspace.

SUMMARY OF THE INVENTION

In general, the instrument and method of the present invention are utilized to remove tissue from an insufflated anatomic cavity though the body wall overlying the endoscopic workspace. The instrument in accordance with the present invention includes an elongate tubular sleeve defining an interior lumen (bore) for removing tissue. The tubular sleeve or "snake" is elastic in transverse sectional dimension so that the interior "snake lumen" can expand to accommodate the excised tissue as it is slidably withdrawn through the lumen. The tubular sleeve herein is called a "snake" because it compares to the body of a snake that stretches in transverse dimension to accommodate any large item that the snake consumes. The snake in accordance with the invention is not elastic in the longitudinal direction in some embodiments due to flexible but non-elastic longitudinal elements integrated into or on a surface of the wall of the snake.

In an exemplary method, assume that the surgeon wishes to remove an excised lymph node from an insufflated workspace overlain by the abdominal wall. Further assume that the insufflated workspace is provided with standard 10 mm. cannulas and the excised tissue has a cross sectional dimension of greater than 10 mm.

The surgeon introduces the snake though one of the cannulas into the workspace. The rigid cannula is then slid outward over the snake leaving only the expandable snake within the abdominal wall. The surgeon then introduces an accessory grasping instrument (e.g., a grasper or snare) though the snake lumen into the workspace. Under endoscopic vision, the surgeon grasps the tissue with the grasper instrument and then draws the tissue outwardly through the snake lumen. As the surgeon uses one hand to stabilize the snake, the excised tissue causes the snake lumen to expand or swell in transverse dimension as it passes through the lumen. As the excised tissue is pulled through the snake into the abdominal wall, the tissue layers in the abdominal wall are displaced radially outward to accommodate the swelled region of the snake. After the excised tissue is disposed outside the abdominal wall but still within the snake lumen, the surgeon or an assistant uses another instrument (e.g., a forceps) to remove the tissue from the lumen through a longitudinal slit in the wall of the snake. Thereafter, the grasping instrument in the snake lumen may be reintroduced into the workspace to remove other pieces of tissue in a like manner. Thereafter, the cannula then easily may be slid inwardly into its original position in the abdominal wall with the snake serving as a guide through the incision and the snake may be withdrawn from the cannula.

In general, the present invention provides an instrument and method for removing excised tissue from an insufflated workspace. The present invention also provides an instrument and method for removing excised tissue having a larger transverse dimension than the bore of a cannula disposed within the body wall overlying the workspace.

The present invention provides an instrument having an interior lumen or passageway that is expandable in transverse dimension to accommodate the cross-sectional dimension of excised tissue. The present invention also provides an instrument and method for removing tissue from a workspace through a small incision that allows the resilience of tissue layers in the body wall to accommodate the proximal movement of excised tissue by transitory radial displacement of the tissue layers surrounding the incision rather than by enlarging the incision.

The present invention provides an instrument and method for removing excised tissue through a cannula without contaminating the cannula valve. The present invention also provides an instrument and method for removing tissue from the interior of the body quickly and efficiently. The present invention also provides an instrument and method that is compatible with existing endoscopic instrumentation.

Additional advantages and features of the invention appear in the following description in which several embodiments are set forth.

BRIEF DESCRIPTION OF THE DRAWINGS

FIG. 1 is an elevational view of a snake device of the present invention including a snake sleeve and a constraining sleeve.

FIG. 2 is an elevational view similar to FIG. 1 with the constraining sleeve in an alternative position.

FIG. 3 is an elevational view of the snake sleeve of FIG. 2 taken along line 3—3 of FIG. 2 showing excised tissue disposed within the lumen in the snake.

FIGS. 8A–8H are sectional views of a patient's abdominal wall illustrating the manner in which a method in accordance with the present invention is practiced utilizing the instrument of FIG. 1.

FIG. 9 is an elevational view of an alternative embodiment of a dual-sleeve snake.

FIG. 10 is an elevational view of the dual-sleeve snake of FIG. 9 in an alternative configuration.

FIGS. 11A–11H are sectional views of a patient's abdominal wall illustrating the manner in which a method in accordance with the present invention is practiced utilizing the instrument of FIG. 8.

FIGS. 12A–12B are enlarged views of a portion of an alternative embodiment of a snake sleeve.

FIG. 13 is an elevational view of a portion of an alternative embodiment of a snake sleeve.

FIG. 14 is an elevational view of the snake sleeve of FIG. 12 with tissue disposed in the lumen of the snake.

FIG. 15 is an elevational view of an alternative embodiment of a tissue recovery sleeve disposed within a snake sleeve.

FIGS. 16A–16B are sectional views of a patient's abdominal wall illustrating the manner in which a method in accordance with the present invention may be practiced utilizing the tissue-recovery sleeve of FIG. 15.

DETAILED DESCRIPTION OF THE INVENTION

Figure 4:
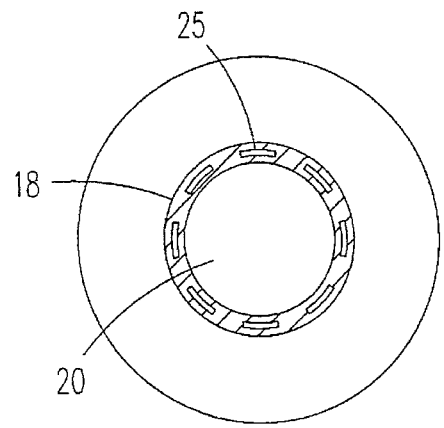
FIG. 4 is a transverse sectional view of the snake sleeve of FIG. 3 taken along line 4—4 of FIG. 3.

By way of example, FIGS. 1 and 2 depict tissue-removing instrument or snake 5 including snake sleeve 10 that is adapted for removing excised tissue from an endoscopic workspace. Snake sleeve 10 with proximal end 11, medial region 12 and distal end 14, is illustrated in FIG. 1 prepared for introduction through a cannula. Snake sleeve 10 has a generally cylindrical shape along longitudinal axis 16 with an overall length of approximately 250 to 500 millimeters (not limiting). The transverse sectional dimension of snake sleeve 10 in a repose state is approximately 10 mm. for introduction through a standard 10 to 11 mm. diameter cannula but such diameter may be any suitable dimension to cooperate with other diameter cannulas.

Figure 5:
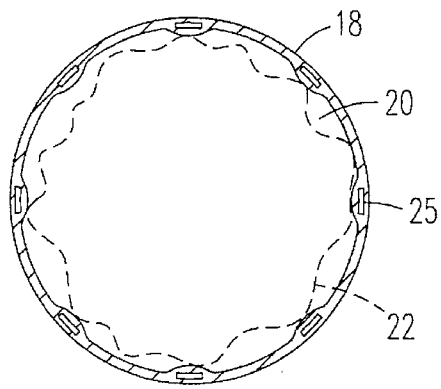
FIG. 5 is a transverse sectional view of the snake sleeve of FIG. 3 taken along line 5—5 of FIG. 3.

Referring to FIGS. 3 and 4, snake sleeve 10 has an interior bore or snake lumen 20 extending along axis 16. The wall 18 of snake sleeve 10 is made of elastomeric material such as latex thus making snake lumen 20 capable of expanding in transverse dimension to accommodate excised tissue 22 as it is pulled through the lumen (see FIGS. 3 and 5). The wall 18 of snake sleeve 10 includes a plurality of longitudinal stiffening elements 25 that may be impregnated within wall 18 or fixed by any suitable means such as adhesives to the inner surface 26 of wall 18 surrounding lumen 20 (see FIG. 4). The stiffeners 25 may be fabricated of any suitable material such as plastic or metal that is not elastic longitudinally but is capable of flexing radially outward from axis 16 as shown in FIG. 3.

The distal end 14 of snake sleeve 10 has a bell (flared) shape 27 that results from the distal ends of stiffeners 25 being resiliently formed in such a bell shape. Such bell-shaped portions of stiffeners 25 overcome the counterforce of the elastomeric material of wall 18 of sleeve 10 to form bell shape 27.

Referring to FIGS. 2–3, the medial region 12 of snake sleeve 10 is configured with one or more longitudinal slits 28 that extend through wall 18 between stiffeners 25 into lumen 20. The proximal end 11 of snake sleeve 10 is provided with a conventional elastomeric seal or gasket 29 (see FIGS. 1–2).

Figure 6:
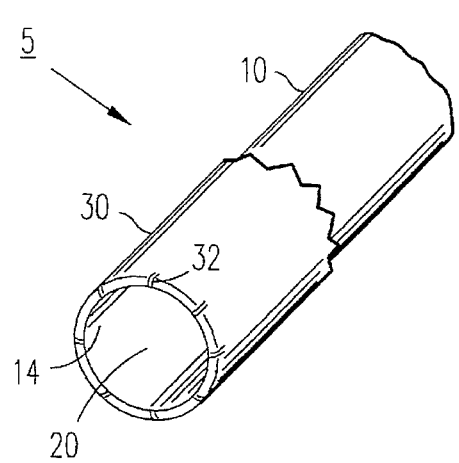
FIG. 6 is an axionometric view of the a portion of the snake device of FIG. 1 taken from along line 6—6 of FIG. 1.
Figure 7:
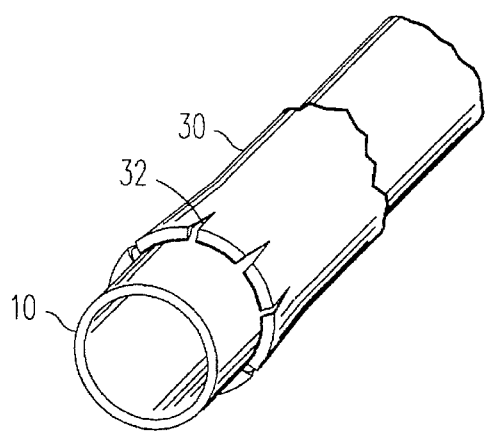
FIG. 7 is an axionometric view similar to FIG. 6 in an alternative configuration.

A constraining sleeve 30 is provided to constrain the bell shape 27 of snake sleeve 10 so that it can be introduced through a cannula. Referring to FIGS. 1–2, constraining sleeve 30 is made of a thin-wall plastic material with a distal end 31 that exhibits a slightly reduced diameter opening to prevent the constraining sleeve from slipping easily in a proximal direction over snake sleeve 10. Referring to FIGS. 6–7, distal end 31 of sleeve 30 has a plurality of weakened-plane longitudinal indentations 32 that will split the distal end of constraining sleeve 30 when it is slid proximally relative to sleeve 10 under force. The proximal end of constraining sleeve 30 has flange 33 for reasons explained hereinbelow.

Operation and use of the instrument of FIGS. 1–2 in performing a method in accordance with the present invention can be described briefly as follows. Assume that the surgeon wishes to remove excised tissue, for example a lymph node, from an endoscopic workspace overlain by the abdominal wall. Assume a 10 mm. diameter cannula is available within the abdominal wall for tissue removal. An endoscope is disposed in another cannula (not shown).

Referring to FIGS. 8A–8H, the abdominal wall has layers of skin 41, tunica adiposa (fat) 42, fascia 44, muscles 45 and peritoneum 49. Referring to FIG. 8A, cannula assembly 50 has longitudinal bore 51. Excised tissue 55 is to be removed from insufflated workspace 56.

Referring to FIG. 8B, snake 5 is provided from the manufacturer with constraining sleeve 30 in its distalmost position so as to constrain bell shape 27 of snake sleeve 10 (see FIG. 1). The surgeon then introduces snake 5 through cannula bore 51 until flange 33 abuts the proximal end of cannula assembly 50. The spacing of flange 33 relative to snake sleeve 10 provides that bell shape 27 of the snake sleeve is distal (inward) from the distal end of the cannula when flange 33 abuts cannula assembly 50.

Referring now to FIG. 8C, the surgeon with one hand (phantom view) holds snake 5 and with the other hand introduces tissue-grasping instrument 60 through gasket 29 and snake lumen 20 into insufflated workspace 56. Instrument 60 is shown with basket-type snare 61 similar to Olympus Model FG-16L-51635, although any type of endoscopic retrieval forceps is suitable.

As also shown in FIG. 8C, the surgeon then pulls proximally (outward) on cannula assembly 50 and removes it from the incision. The proximal movement of cannula 50 also causes constraining sleeve 30 to move proximally as flange 33 abuts the cannula. The proximal movement of sleeve 30 thus allows bell shape 27 to expand within workspace 56. As shown in FIG. 8C, the surgeon leaves the cannula generally fitted around proximal end 11 of snake sleeve 10. Alternatively, the surgeon may entirely remove the cannula from its sliding fit over snake 5 and set it aside. It also should be noted that the steps shown in FIGS. 8B and 8C may be reversed with the surgeon first introducing grasping instrument 60 into snake lumen 20 and then sliding the assembly through cannula 50.

Referring to FIG. 8D, the surgeon then recovers tissue 55 in snare 61 under endoscopic vision, utilizing another accessory instrument in another cannula (not shown) if necessary. FIG. 8D depicts tissue 55 in snare 61 being pulled through bell shape 27 which causes the distal end 14 of the snake sleeve 20 to expand radially.

In FIG. 8E, tissue 55 is shown as it is pulled through the abdominal wall which causes snake lumen 20 to expand in transverse dimension, in turn causing muscle layer 45, fascia 44 and fat layer 42 to be displaced radially outward from axis 16 of the snake. The resilience of tissue layers in the abdominal wall allows excised tissue 55 to pass therethrough without tearing tissue layers or significantly enlarging the dimensions of the incision.

In FIGS. 8F–8G, excised tissue 55 is outside the abdominal wall still in lumen 20. The surgeon or his assistant then may pull tissue 55 through slit 28 in wall 18 with forceps 65. Note that in FIG. 8G, a portion of medial region 12 of snake sleeve 20 may be configured with a thin wall portion 66 including a cooperating pattern of slits 28 such that sleeve 10 will collapse under the pressures of the abdominal wall thereby preventing substantial leakage of insufflation gases from the workspace when instrument 60 is not within lumen 20. Snake sleeve 10 then may be reintroduced into workspace 56 to remove other tissue in a like manner. As shown in FIG. 8H, upon completion of the tissue removal procedure, cannula 50 then easily may be slid distally (inward) into its original position in the abdominal wall with snake sleeve 10 serving as a guide through the incision. Thereafter, snake 5 and accessory instrument 60 may be withdrawn leaving cannula 50 in place.

The above-described snake 5 utilizes a single sleeve 10 wherein excised tissue 55 is recovered and pulled through snake lumen 20 with a grasping instrument. In some situations, it may be difficult to grasp tissue 55 or to maintain a grip on the tissue as it is pulled through snake lumen 20. For this reason, FIGS. 9–10 depict an alternative embodiment of snake 105 with dual sleeves. Alternative snake sleeve 110 with proximal and distal ends 111 and 114 is similar to the embodiment previously described having wall 118 made of elastomeric material and having lumen 120 along with stiffening elements 125 (see FIG. 10).

Snake device 105, however, includes a separate tissue-recovery sleeve 130 adapted for pulling tissue through lumen 120. Referring to FIG. 10, recovery sleeve 130 with proximal end 131 has longitudinal tissue-recovery passageway 132 extending therethrough which is dimensioned to receive an accessory grasping instrument as well as tissue 55. The proximal end 131 of sleeve 130 has a conventional elastomeric gasket 133. The distal region 134 of sleeve 130 and passageway 132 are capable of expanding in transverse dimension to accommodate excised tissue similar as previously-described. Longitudinal stiffeners 135 incorporated into wall 138 of sleeve 130 induce bell shape 139 into the distal end of the recovery sleeve. As can be seen in FIGS. 9–10, the distal end of recovery sleeve 130 can be withdrawn into snake sleeve 110 thus constraining bell shape 139 for introduction of snake 105 through a cannula.

Of particular interest to dual sleeve snake 105 is that excised tissue 55 will not itself cause friction with inner surface 140 of snake lumen 120 as the tissue is pulled through the lumen. In dual sleeve snake 105, the sliding interface between snake sleeve 120 and recovery sleeve 130 is inner surface 140 of lumen 120 in contact with outer surface 142 of recovery sleeve 130. Friction between surfaces 140 and 142 can be reduced by using "slippery" materials for the respective surfaces, for example slippery elastomeric materials. Alternatively, stiffeners 125 and 135 may be partly or wholly exposed in the respective surfaces of the sleeves and such stiffeners may be fabricated from slippery materials such as Teflon.

Figure 11A:
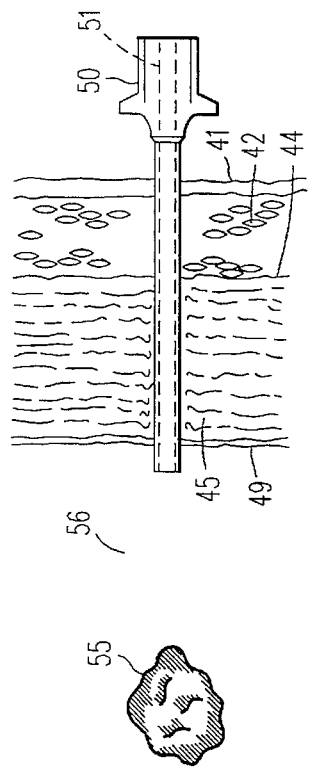
Figure 11B:
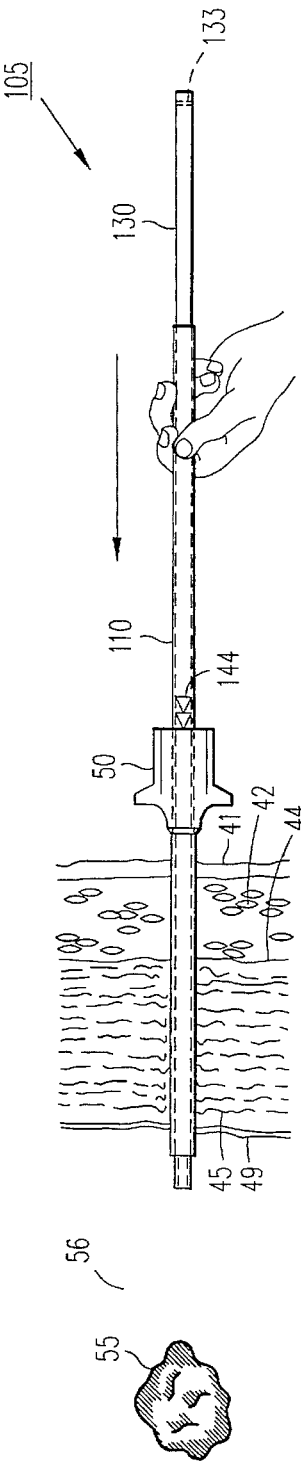

Operation and use of the instrument of FIGS. 9–10 in performing the method of the invention can be described briefly as follows. Referring to FIG. 11A, assume again that the surgeon wishes to remove excised tissue 55 from a workspace overlain by the abdominal wall. Referring to FIG. 11B, the surgeon introduces snake 105 through cannula bore 51. An indicator mark 144 on snake sleeve 110 indicates when the distal end of sleeve 110 is distal (inward) from the distal end of the cannula.

Figure 11C:
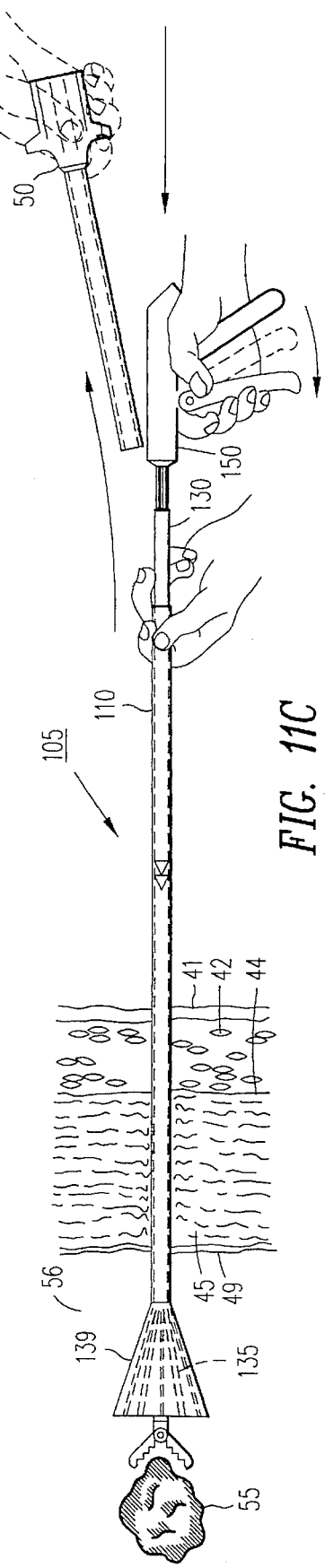

Referring now to FIG. 11C, the surgeon with one hand (phantom view) slides the cannula proximally (outward) over the snake device 105 and sets it aside. The surgeon then introduces grasping instrument 150 through gasket 133 and passageway 132 in recovery sleeve 130 into insufflated workspace 56. It should be noted that the steps shown in FIGS. 11B and 11C may be reversed with the surgeon first introducing instrument 150 into snake 105 and then sliding the assembly through cannula 50.

Under endoscopic vision as shown in FIGS. 11C–11D, the surgeon grasps tissue 55 and pulls it proximally (outward) into bell shape 139 and passageway 132 of sleeve 130. In FIG. 11E, the tissue is being pulled through the abdominal wall which displaces radially outwardly portions of walls 18 and 118 of sleeves 120 and 130, respectively, as well as muscle layer 45, fascia 44 and fat layer 42. As shown in FIGS. 11F–11G, it is preferable to withdraw grasper 150 after tissue 55 is within bell shape 139 of recovery sleeve 130. Thereafter, the surgeon may simply grip and pull on proximal end 131 of recovery sleeve 130 to pull the tissue through snake sleeve 110.

After recovery sleeve 130 is fully withdrawn proximally from snake sleeve 110 as shown in FIG. 11H, the cannula 50 may be slid distally (inward) over snake sleeve 110 back into the incision using snake sleeve 110 as a guide. It should be noted in FIG. 11H that the surgeon may use his thumb and fingers to collapse snake sleeve 110 to prevent insufflation gases from escaping from workspace 56 through snake lumen 130. Alternatively, the proximal end of snake sleeve may be fitted with a conventional elastomeric gasket (not shown).

It can be seen that the snake sleeves, 10 and 110, in the above-described embodiments are similar. Other embodiments of expandable snake sleeves incorporating additional features are illustrated in FIGS. 12–15 and such features are suitable for either single-sleeve or dual-sleeve snakes.

Referring to FIGS. 12A–12B, additional structure may be provided for making a snake sleeve 200 with an enhanced ability to expand in the transverse dimension. Such enhanced expansion ability assists in displacing abdominal wall tissue radially outward to accomplish the manner of operation of a snake sleeve. FIGS. 12A–12B depict stiffening elements 205 disposed helically around wall 208 of snake sleeve 200. As tissue is pulled through lumen 210, the helical stiffening elements, depending on their spiral lead dimension 211, will tend to move somewhat helically in expanding radially outward as tissue is pulled though the lumen. In other words, axial forces on tissue in lumen 210 will be transformed partly into helical forces (radial and angular) within wall 208 that in turn displace abdominal wall tissue layers radially outward in an efficient manner. A similar snake sleeve (not shown) may have cooperating right-hand and left-hand helical elements.

Referring to FIG. 12A, structure is provided for allowing snake sleeve 200 to grip the abdominal tissue surrounding the sleeve. The purpose of a snake sleeve gripping surrounding tissue is to insure that the surgeon does not have to apply distal counterforce on the snake sleeve as proximal force is applied to pull tissue through the snake lumen. For example, exterior surface 212 of sleeve 200 may have gripping ribs 215 molded into the material of wall 208 to prevent it from sliding proximally in tissue. Alternatively, the elastomeric material in wall 208 may be a somewhat "sticky" material that resists sliding through the tissue of the abdominal wall.

Referring to FIGS. 13–14, interwoven snake sleeve 220 has helical stiffening elements made e.g. of thin flat plastic that are loosely interwoven in opposing right-hand spirals 222a and left-hand spirals 222b. Thus, withdrawal of tissue through such interwoven sleeve 220 causes lumen 225 to increase the transverse dimension as both helical elements counter-rotate relative to one another thus effectively changing the spiral lead 229 of the elements, wherein the spiral lead is defined as the axial dimension required for a helical element to wrap 360° around sleeve 220. In such an interwoven sleeve 220, the helical elements alone may make up a suitable snake sleeve in which case the elastomeric sleeve 230 depicted in phantom view is optional (see FIGS. 13–14).

FIG. 15 illustrates a dual-sleeve snake 235 with snake sleeve 240 having its distal end slidably disposed distally (outward) from tissue-recovery sleeve 245. Structure is provided for making recovery sleeve 245 slide with reduced resistance through snake lumen 250. Recovery sleeve 245 is formed of a plurality of right-hand and left-hand helical elements, 251a and 251b, that are made of thin strips of slippery material such as Teflon that slides easily within snake lumen 250. In the distal portion of sleeve 245, the helical elements are resiliently formed in bell shape 252 in a state of repose. The distal portion of the sleeve is capable of both expanding and contracting in transverse sectional dimension as spiral lead 253a changes (see phantom views in FIG. 15).

Still referring to FIG. 15, the dual-sleeve snake 235 also includes structure incorporated into recovery sleeve 245 for gripping and compressing excised tissue 55 inwardly toward axis 254. The purpose of gripping the tissue is to insure that when tissue 55 is first pulled into the passageway 255 with a grasper, the grasper may be removed and the tissue will not move distally out of passageway 255 when recovery sleeve 245 is pulled proximally. The purpose of compressing tissue 55 in the cross-sectional dimension is to make it easier to pull the tissue through lumen 250 in snake sleeve 240. In other words, the snake sleeve will require less expansion to accommodate the lesser cross section of tissue 55, in turn requiring less displacement of tissue in the abdominal wall. Thus, pulling proximally on proximal end 256 of recovery sleeve 245 will cause interwoven sleeve 245 to reduce its transverse sectional dimension whereby passageway 255 will both grip and compress excised tissue 55 as it is pulled into snake lumen 250. In this embodiment, wall 258 snake sleeve 240 may be fabricated of a more rigid elastomeric material than previously described to assist the recovery sleeve 245 in compressing tissue.

Of particular interest to the present invention is that tissue-compressing recovery sleeve 245 of FIG. 15 may be utilized alone to remove certain soft or malleable tissues through a rigid cannula assembly. Referring to FIGS. 16A–16B, operation and use of only recovery sleeve 245 alone in performing a method in accordance with the invention can be described briefly as follows. Referring to FIG. 16A, assume again that the surgeon wishes to remove excised tissue 55 from a workspace overlain by the abdominal wall. FIG. 16A depicts the surgeon introducing recovery sleeve 245 through cannula assembly 50 into workspace 56 (the constraining sleeve not shown). Grasping instrument 260 is introduced through tissue-recovery passageway 255 in recovery sleeve 245 to grasp tissue 55. As the tissue is pulled into the distal bell shape 252 of sleeve 245, the sleeve and passageway 255 naturally expand in transverse dimension to decrease spiral lead 253b of elements 251a and 251b until passageway 255 has a large enough transverse dimension to accommodate tissue 55 (see phantom view in FIG. 16A). After tissue 55 is disposed within passageway 255, the grasping instrument 260 is withdrawn. Thereafter, as shown in FIG. 16B, recovery sleeve 245 is pulled through bore 51 in cannula 50. As sleeve 245 is pulled proximally, the helically interwoven sleeve first grips tissue 55 and thereafter compresses the soft tissue as it is drawn into the cannula. The proximal sliding of sleeve 245 into cannula 50 causes the interwoven elements to interact so as to lengthen spiral lead 253c of helical elements 251a and 251b as the transverse sectional dimension of sleeve 245 is constrained by the reduced dimension of bore 51 of the cannula. In so doing, the helical interaction of elements 251a and 251b stretches tissue 55 axially since the helical elements frictionally engage tissue 55 within passageway 255. Such stretching of tissue 55 serves to reduce the cross-sectional dimension along with compressing the tissue to make it easier to pull the tissue through the rigid cannula. Another grasper (not shown) may be introduced through another cannula to pull distally on the distal end of helical elements 251a and 251b which will further compress tissue 55 within passageway 255 as recovery sleeve 245 is pulled through the rigid cannula.

Although the instrument and method of the present invention has been described for removing excised tissue from an insufflated workspace through the abdominal wall, the invention may be used in conjunction with tissue removal from any location in the body in which a cannula is disposed, whether or not the space is insufflated. This disclosure is illustrative and not limiting; further variations will be apparent to one skilled in the art in light of this disclosure and are intended to fall within the scope of the appended claims.

I claim:

1. An instrument for removing excised tissue from the interior of a body through an incision for a cannula and for guiding a cannula into and of said incision, comprising:

an elongate tubular sleeve having proximal and distal ends and a medial portion, a sleeve wall defining an interior bore extending therethrough;

an exterior of the tubular sleeve having a first repose position with a first transverse dimension, at least a portion of said tubular sleeve being capable of a second tensioned position with an expanded second transverse dimension;

wherein at least a portion of said interior bore expands in its transverse dimension when the tubular sleeve moves to said second tensioned position from said first repose position to accommodate a cross section of excised tissue pulled through said bore to a location exterior of the body;

wherein the instrument with the tubular sleeve in the repose position is capable of being passed through the bore of said cannula thereby serving as a guide to introduce said cannula into and out of said incision;

wherein said sleeve wall comprises a plurality of flexible elements including a first set disposed in a right-hand helical configuration and a second set disposed in a left-hand helical configuration and said first and second sets are interwoven.

2. A surgical instrument for removal of excised tissue from an endoscopic workspace, comprising:

an elongate sleeve having proximal and distal ends and a medial portion, a sleeve wall defining an interior bore wherein said bore expands and contracts in its transverse sectional dimension to accommodate a cross section of excised tissue pulled through said bore;

wherein said sleeve wall comprises a plurality of flexible elements including a first set disposed in a right-hand helical configuration and a second set disposed in a left-hand helical configuration and said first and second sets are interwoven.

3. The instrument of claim 2 wherein said sleeve wall is an elastomeric material.

4. The instrument of claim 2 wherein said sleeve wall is a plurality of flexible stiffening elements.

5. The instrument of claim 4 wherein said plurality of flexible elements are disposed longitudinally to said sleeve wall.

6. The instrument of claim 4 wherein said plurality of flexible elements are disposed helically to said sleeve wall.

7. The instrument of claim 2 wherein said sleeve wall includes an elastomeric component.

8. The instrument of claim 2 wherein said distal end of said tubular sleeve has a flared shape in a first repose position and is resiliently deformable to a cylindrical shape in a second tensioned position.

9. The instrument of claim 8 wherein the flared shaped repose position is induced by a plurality of resiliently formed flexible elements included in said sleeve wall.

10. The instrument of claim 8 together with a constraining sleeve slidably mounted around said tubular sleeve, wherein said flared shape of said tubular sleeve is maintained in either said repose position or said tensioned position by the slidable disposition of said constraining sleeve.

11. The instrument of claim 2 wherein said tubular sleeve defines at least one longitudinal slit in said tubular sleeve within said medial portion of said tubular sleeve.

12. An instrument for removing excised tissue from the interior of a body through an incision for a cannula and for guiding a cannula into and of said incision, comprising:

an elongate tubular sleeve having proximal and distal ends and a medial portion, a sleeve wall defining an interior bore extending therethrough;

an exterior of the tubular sleeve having a first repose position with a first transverse dimension, at least a portion of said tubular sleeve being capable of a second tensioned position with an expanded second transverse dimension;

wherein at least a portion of said interior bore expands in its transverse dimension when the tubular sleeve moves to said second tensioned position from said first repose position to accommodate a cross section of excised tissue pulled through said bore to a location exterior of the body;

wherein the instrument with the tubular sleeve in the repose position is capable of being passed through the bore of said cannula thereby serving as a guide to introduce said cannula into and out of said incision; and wherein said sleeve wall comprises a plurality of flexible elements including a first set disposed in a right-hand helical configuration and a second set disposed in a left-hand helical configuration and said first and second sets are interwoven;

and further comprising:

an elongate inner sleeve slidably carried within said interior bore of said tubular sleeve, the inner sleeve having a proximal end and a distal portion with a second sleeve wall defining an interior second bore extending therethrough, wherein at least the distal portion of said second bore is capable of expansion in its transverse sectional dimension to accommodate the cross section of said excised tissue recovered within said second bore.

13. The instrument of claim 12 wherein said second bore in the distal portion of said inner sleeve has an increasing transverse sectional dimension in the distal direction in a repose position and is resiliently deformable to a cylindrical shape in a tensioned position.

14. The instrument of claim 13 wherein the distal portion of said inner sleeve wall includes a plurality of flexible elements including a first set disposed in a right-hand helical configuration and a second set disposed in a left-hand helical configuration, and said first and second sets are interwoven.

15. A method for removing excised tissue from the interior of the body through a body wall wherein said excised tissue has a greater transverse dimension than an incision for a cannula through said body wall, utilizing an elongate tubular sleeve defining an interior bore capable of repose and expanded positions, comprising the steps of:

introducing a distal portion of said tubular sleeve through the cannula disposed in said incision through said body wall;

withdrawing proximally the cannula from said incision over said tubular sleeve, thereby leaving said tubular sleeve in said body wall;

advancing a tissue-engaging instrument through said bore in said tubular sleeve;

engaging the tissue with said instrument;

pulling the tissue proximally through said bore in said tubular sleeve thereby causing said bore to expand in its transverse sectional dimension to an expanded position to accommodate the proximal movement of said excised tissue, thereby displacing tissue in the body wall surrounding said tubular sleeve radially outward to accommodate the proximal movement of said excised tissue; and re-introducing the cannula back into said incision over said tubular sleeve thereby using said tubular sleeve as a guide for the cannula.

16. The method of claim 15 wherein said tubular sleeve defines at least one slit in a wall of its medial portion, further comprising the step of removing said excised tissue from said bore through said slit.

17. The method of claim 15 further comprising the step of removing said excised tissue from said bore through a proximal end of said bore.

18. The method of claim 15 wherein after said excised tissue has been removed from said bore, further comprising the step of withdrawing said tubular sleeve from said cannula.

19. A method for removing excised tissue from the interior of the body, said excised tissue having a greater transverse dimension than the incision providing access to the interior of the body utilizing an instrument comprising an outer first sleeve and a cooperating inner sleeve, wherein said outer and inner sleeves define respective first and second interior bores, comprising the steps of:

introducing a distal portion of the instrument through a cannula disposed within a body wall into the interior of the body to the location of said excised tissue;

positioning said excised tissue within the distal portion of said second bore with an accessory instrument;

pulling the inner sleeve with said excised tissue disposed therein proximally through the first bore;

causing said first and second bores to expand in their transverse sectional dimension to accommodate the proximal movement of said excised tissue, thereby displacing tissue in said body wall surrounding said outer and inner sleeves radially outward to accommodate the proximal movement of said excised tissue; and reintroducing the cannula back into the incision over said outer sleeve thereby using said outer sleeve as a guide and thereafter withdrawing said outer sleeve from the cannula.

20. The method of claim 19, wherein said step of positioning comprises:

sliding a tissue-engaging instrument distally through the second bore; and engaging and transporting said excised tissue into the distal portion of said second bore.

21. The method of claim 19, wherein said step of positioning comprises:

introducing an accessory instrument into the exterior of the body through the cannula; and pushing the excised tissue with the necessary instrument into the distal portion of said second bore.

22. A surgical instrument for removal of excised tissue from an interior of a body, comprising:

an elongate first sleeve having proximal and distal ends and a medial portion, a sleeve wall defining an interior bore wherein said bore expands and contracts in its transverse sectional dimension to accommodate a cross section of excised tissue pulled through said bore; and an elongate inner sleeve dimensioned for slidable disposition within said interior bore of said first sleeve, and having a proximal lend and a distal portion, a second sleeve wall defining an interior second bore extending therethrough, wherein the distal portion of said second bore expands and contracts in its transverse sectional dimension to accommodate the cross section of said excised tissue recovered within said second bore;

wherein said interior second bore in the distal portion of said inner sleeve has an increasing transverse sectional dimension in the distal direction in a repose position and is resiliently deformable to a cylindrical shape in a tensioned position.

* * * * *